US009108074B2

(12) United States Patent
Rittner et al.

(10) Patent No.: US 9,108,074 B2

(45) Date of Patent: Aug. 18, 2015

(54) CHEMICAL OXYGEN GENERATOR WITH CORE CHANNEL TUBE FOR AN EMERGENCY OXYGEN DEVICE

(75) Inventors: Wolfgang Rittner, Ahrensbok (DE); Rudiger Meckes, Berkenthin (DE)

(73) Assignee: Zodiac Aerotechnics, Plaisir (FR)

( * ) Notice: Subject to any disclaimer, the term of this patent is extended or adjusted under 35 U.S.C. 154(b) by 0 days.

(21) Appl. No.: 13/358,611

(22) Filed: Jan. 26, 2012

(65) Prior Publication Data

US 2013/0192596 A1 Aug. 1, 2013

(51) Int. Cl.

| | |
|---|---|
| ***A61M 15/00*** | (2006.01) |
| ***A61M 16/00*** | (2006.01) |
| ***A62B 7/00*** | (2006.01) |
| ***A62B 21/00*** | (2006.01) |
| ***A62B 7/08*** | (2006.01) |
| *A62B 7/14* | (2006.01) |

(52) U.S. Cl.

CPC . *A62B 21/00* (2013.01); *A62B 7/08* (2013.01); *A62B 7/00* (2013.01); *A62B 7/14* (2013.01)

(58) Field of Classification Search

None

See application file for complete search history.

(56) References Cited

U.S. PATENT DOCUMENTS 2,507,450 A * 5/1950 Millikan et al. ......... 128/202.26
3,536,456 A 10/1970 Bovard
3,573,001 A * 3/1971 Bovard ......................... 422/120
3,580,250 A * 5/1971 Oroza ...................... 128/202.26
3,736,104 A * 5/1973 Churchill et al. ............. 422/120
3,868,225 A * 2/1975 Tidd ............................. 422/122
4,197,213 A * 4/1980 Pietz et al. ..................... 252/372
4,246,229 A * 1/1981 McBride et al. .............. 422/122
4,278,637 A * 7/1981 McBride ....................... 422/122
4,891,189 A * 1/1990 Harwood, Jr. ................ 422/165
5,042,471 A * 8/1991 Drews et al. ............. 128/202.26
5,322,669 A * 6/1994 Bechthold et al. ............ 422/120
5,804,146 A * 9/1998 Heyer et al. ................... 422/126
6,155,254 A * 12/2000 Evrard et al. ............ 128/202.26
7,513,251 B2 * 4/2009 Blum ....................... 128/202.26

FOREIGN PATENT DOCUMENTS

GB 2035808 * 6/1980 ............. A62B 19/02
GB 2035808 A 6/1980
JP H05270804 A 10/1993

OTHER PUBLICATIONS

Thomas, Martin A, Porous Problems: Ceramics and Structural Materials, Quantachrome Corporation, 2010, p. 1.*
European Search Report issued in EP Publication No. 2620182 on Feb. 25, 2014, 11 pages.

* cited by examiner

*Primary Examiner* — Tan-Uyen (Jackie) T Ho
*Assistant Examiner* — Eric Bryant
(74) *Attorney, Agent, or Firm* — Kilpatrick Townsend & Stockton LLP; Dean W. Russell; Kristin M. Crall

(57) ABSTRACT

Embodiments of the invention relate to a chemical oxygen generator for an emergency oxygen device, comprising an outer housing defining an interior space and comprising an outlet opening, a solid oxygen source within said interior space containing a material which is able to produce oxygen in a chemical reaction. According to embodiments of the invention, a hollow tube within said interior space is embedded in said solid oxygen source.

15 Claims, 2 Drawing Sheets

CHEMICAL OXYGEN GENERATOR WITH CORE CHANNEL TUBE FOR AN EMERGENCY OXYGEN DEVICE

FIELD OF THE INVENTION

Embodiment of the invention relate to a chemical oxygen generator for an emergency oxygen device, comprising an outer housing defining an interior space and comprising an outlet opening, a solid oxygen source within said interior space containing a material which is able to produce oxygen in a chemical reaction. A further aspect of the invention is an emergency oxygen device, comprising such an chemical oxygen generator.

BACKGROUND

Chemical oxygen generators of this type are used as an alternative to oxygen pressure tanks in emergency oxygen devices installed on board of civil aircraft mainly. These emergency oxygen devices serve to supply oxygen to passenger or cabin crew in case of an emergency situation like a decompression situation. In such a situation an oxygen flow is provided to an oxygen mask which can be worn by the passenger in order to allow him constant breathing and sufficient uptake of oxygen for his vital functions.

It is known in the prior art to include a chemical oxygen generator in such an emergency oxygen device as a source of oxygen. Such chemical oxygen generators include a solid material serving as the oxygen source such as sodium chlorate which can produce oxygen in a chemical reaction with iron. This chemical reaction is started in case of an emergency situation, e.g. by the passenger pulling the mask to himself and thus actuating a respective switch whereby a pyrolytic reaction is started in a pyrolytic ignition unit effecting local heating of the solid material in a starting region. In this starting region, the chemical reaction begins which is exothermic and thus causes the solid material to continuously react in a chemical reaction and produce oxygen in a gaseous state.

A first problem associated with such emergency oxygen devices utilizing a chemical oxygen generator is the procedure of starting the chemical reaction which requires a specific interaction of mechanical and pyrolytic components. This interaction is prone to misuse and maloperation and can not be adapted to modern cabin control systems with regard to maintenance and safety conditions.

A second problem associated with such emergency oxygen devices utilizing chemical oxygen generators is the non-constant production of oxygen as a result of the chemical reaction. Generally, a delayed production of oxygen occurs after ignition and initial start of the chemical reaction. Hereafter, in a first phase of the chemical reaction, only a small volume of oxygen is produced which is in particular unfavorable because the aircraft may at this time be in high altitude flight level wherein a decompression situation within the cabin requires a high amount of oxygen to be supplied to the passengers to maintain their vital functions. Hereafter, in a later stage of the chemical reaction, a large volume of oxygen is produced because the chemical reaction is fully activated in the solid material. However, in this second stage the aircraft may have descended to a low altitude flight level in order to relieve the decompression situation and the passenger may only require a small amount of oxygen at this flight level. However, given a situation where the decompression situation occurs in a long distance to the nearest suitable airport, the aircraft may expect a long flight time until it reaches the airport and thus it would be ideal to supply a small amount of oxygen over a long time to the passenger. It is an object of the invention to improve the delivery rate of oxygen by an emergency oxygen system with regard to these conditions.

In a first approach, it is known in the prior art to include an oxygen pressure tank in an emergency oxygen device storing oxygen in a pressurized state. Using such pressurized oxygen it is possible to immediately supply a large amount of oxygen to the passenger in an emergency situation and to reduce this supply by a respective control valve in a later stage of the continuing emergency situation when flying at low altitude flight level. It is further known to combine such an oxygen pressure tank with a chemical oxygen generator in an emergency oxygen device to allow immediate supply of oxygen out of the pressure tank in the first stage of the emergency situation and to provide oxygen for a long time out of the chemical oxygen generator in a later stage. However, a major draw back of these systems is the need to handle high pressures within the emergency oxygen system with requires continuous safety checks and maintenance of the system to ensure proper function of the system. Further, such oxygen pressure tanks must be completely sealed in order to hold the required amount of oxygen inside and a leakage of oxygen out of such tanks is very dangerous in that the air inside the aircraft may be enriched with oxygen and thus the risk of fire on board the aircraft is increased. A further draw back of such systems is the significant weight of such a pressure tank which is caused by the wall thickness required for bearing the high inner pressure inside the tank.

Generally, the oxygen flow out of a chemical oxygen generator may be regulated using a control valve to compensate for some of the problems associated with such chemical oxygen generators. However, this causes significant disadvantages in the system. First, by throttling the oxygen flow the pressure inside the chemical oxygen generator will significantly increase and this requires the housing of the oxygen generator to be configured to take up such inner pressure. By this, a significant advantage of chemical oxygen generators, namely its low weight, is sacrificed. Secondly, such increase of pressure inside the chemical oxygen generator will inadvertently influence the chemical reaction and may result in a reduction of the reaction. This, however, makes its difficult to control the oxygen flow and in particular produces the risk that the chemical reaction is stopped or reduced to a degree which is not sufficient for the production of enough oxygen for the passenger.

BRIEF SUMMARY

It is an object of the invention to overcome these problems and to provide an improved emergency oxygen device for use on board of an aircraft.

This object is solved by a chemical oxygen generator as described in the introductory portion comprising a hollow tube within said interior space embedded in said solid oxygen source.

The chemical oxygen generator according to the invention comprises a hollow tube which is surrounded by said solid oxygen source. The hollow tube may have any cross sectional area, in particular a circular cross section, rectangular cross section, polygonal cross section or the like. The hollow tube allows first for optimizing the surface of the solid oxygen source which improves the rate of oxygen production in all stages of the chemical reaction because an additional contact area is provided by said hollow tube. Further, the hollow tube improves the manufacturing technique of the solid oxygen source in that it allows the solid oxygen source to be compressed in an isostatic pressure technique around the hollow tube, thus allowing to improve the homogeneity and density of the solid oxygen source. Further, the hollow tube provides a path for heat transfer within the solid oxygen source thus effecting a more constant chemical reaction in the solid oxygen source volume and a quicker startup of the chemical reaction after ignition.

According to a first embodiment, said outer housing defines a longitudinal direction and a transversal direction and has a larger extension in longitudinal direction than in transversal direction and wherein said hollow tube extends along the longitudinal direction, preferably from one end of the housing to the other end in said longitudinal direction. The outer housing may in particular the shaped like a cylinder or drum having an axial extension which is larger than the diameter of said cylinder or drum. It is preferred that the hollow tube extends in said axial direction corresponding to the longitudinal direction as explained before hand. It is to be understood that the chemical oxygen generator may have other cross sectional geometries and that the hollow tube may extend through said housing in an orthogonal direction or oblique or in an angled direction with respect to the cross sectional plane of said housing. Generally, it is preferred to provide a sufficient length of the hollow tube in order to transfer a sufficient amount of heat into the solid oxygen source from said hollow tube by heat conduction out of said tube wall or heat transfer from oxygen flowing through the tube.

According to a further embodiment, said tube is made from metal. Generally, it is to be understood that the tube may be made of any material which is adapted to with stand the temperature inside the chemical oxygen generator. The material may be adapted to with stand the chemical reaction or may be adapted to participate in said chemical reaction partly or completely. In a specific embodiment, the material may be adapted to degrade by said chemical reaction partly or completely in order to improve the delivery rate of the oxygen out of the oxygen generator over its time of operation.

Still further, it is preferred that said tube comprises a plurality of radial openings. By providing such a plurality of radial openings, e.g. by using a perforated tube or a tube having a plurality of slits in its wall or the like, oxygen produced by the chemical reaction of the solid oxygen source may enter through said openings into the interior space defined by said hollow tube. The oxygen may enter said interior space at any point of the tube where such radial opening is provided in the tube wall. By this, the oxygen may flow inside the tube and thus effect a quick and effective heat transfer within the chemical oxygen generator resulting in a constant chemical reaction and a quick start up of the chemical reaction.

According to a further embodiment, said hollow tube and said solid oxygen source extend from a first end of said housing to a second end of said housing and a starter unit for initiating a chemical reaction in said solid oxygen source is provided at said first end and said outlet opening is located at said second end. According to this embodiment, the chemical reaction is started at a maximum distance from the outlet opening thus allowing the oxygen to flow through the whole length of the housing and to thus dissipate a maximum of heat into the solid oxygen source along this flow path. Further, this embodiment is advantageous since the ignition process is separated from the outlet opening thus enhancing safety since any electronic units like a control valve arranged close to the outlet opening does not interfere with the starter unit and is not effected by heat transfer there from or the like.

According to an alternative embodiment, said hollow tube and said solid oxygen source extend from a first end of said housing to a second end of said housing and a starter unit for initiating a chemical reaction in said solid oxygen source and said outlet opening are mounted at the first end of the housing. In this embodiment, the oxygen produced by the chemical reaction may flow directly from the starting point of this reaction to the outlet opening and the hollow tube may only serve to take up some of this oxygen in order to distribute and dissipate heat in the other regions of the solid oxygen source being arranged at a distance from said first end of the housing. Further, in this embodiment the hollow tube may be configured such that it comprises two separate flow paths sections connected to each other at the second end of the tube, e.g. by using a hollow tube having a two chamber cross section. Using such a hollow tube the oxygen produced by the chemical reaction may enter into one flow path within said tube, e.g. through radial openings in the hollow tube provided in the outer wall of said first flow path section. The oxygen may than flow through said first flow path section and change its direction at the second end to flow through the second flow path section and return to the first end to exit the housing through the outlet opening. Using this embodiment, the flow path of the oxygen is extended thus effecting more heat transfer out of the oxygen into the solid oxygen source.

According to a further embodiment a hollow space, preferably a ring-shaped space, is located between said solid oxygen source and said housing wherein said hollow space is preferably in fluid communication with the interior of said hollow tube. Said hollow space may be of different geometry and may e.g. include a plurality of interconnected or separated spaces, e.g. by providing a solid oxygen source having a cross section with a polygonal outer geometry or a star-like cross section or the like. Generally, due to the solid oxygen source being arranged to surround the hollow tube it is not required in the oxygen generator according to the invention that the solid oxygen source is in contact to the housing of the oxygen generator since a safe and proper fixation of said solid oxygen source can be achieved by fixing the hollow tube to the housing and attaching the solid oxygen source to the hollow tube. This allows for significant improvements. First, such hollow space between the solid oxygen source and the housing prevents the housing to be heated to high temperatures following a direct contact to the solid oxygen source and the chemical reaction of it. This allows to reduce the efforts made for thermal insulations of the oxygen generator and the space required for such insulation. Further, such hollow space may be used to direct oxygen along the outer surface of the solid oxygen source in order to transfer heat into the solid oxygen source and thus influence and improve the chemical reaction and the delivery rate of oxygen out of said chemical reaction. Further, the start up of the chemical reaction can be improved significantly hereby.

In particular, it is preferred, when using an oxygen generator having the starter unit and the outlet opening at the same end of the housing and the hollow space as described before hand, that said fluid communication between said hollow space and said hollow tube is provided at a second end of the housing which is opposed to the first end. In such case, a flow path of the oxygen can be established at the beginning of the chemical reaction which includes the whole hollow tube and the whole hollow space by directing said oxygen from the first and to the second end and back to the first end to the outlet opening. This will significantly increase the heat transfer from the oxygen into the solid oxygen source and thus result in a significant shortening of the start up time of the oxygen generator.

Still further, it is preferred that a filter for filtering chlorine is integrated into said hollow tube. Usually, using sodium chlorate as solid oxygen source, a reaction of this sodium chlorate with iron will produce sodium chloride, iron oxide and oxygen. However, the sodium chloride has to be filtered out of the gas produced by the chemical reaction to prevent injury to the passenger. By incorporating such filter for filtering this sodium chloride or chlorine out of the gas into the hollow tube the oxygen generator can be significantly reduced in length and a compact design of an emergency oxygen device is achieved.

The oxygen generator according to an embodiment of the invention may further preferably be constructed in such a way that said hollow tube is embedded in said solid oxygen source and perforated to allow oxygen to enter out of said solid oxygen source into the interior space of said hollow tube, said solid oxygen source extends from a first end to a second end along said hollow tube, a starter unit for initiating a chemical reaction of said solid oxygen source is provided at the first end of said solid oxygen source, a hollow space is provided between said solid oxygen source and said housing, said hollow space being in fluid communication with the interior of said hollow tube at the second end of said solid oxygen source to direct oxygen from said interior of said hollow tube into said hollow space, and said outlet opening is located at the first end of the solid oxygen source and is in fluid communication with said hollow space.

Using such a configuration an improved, shorted start up of the chemical reaction with immediate delivery of a sufficient rate of oxygen is achieved. At the same time, the chemical oxygen generator can be build in a compact design and a high temperature of the housing is prevented during said chemical reaction.

According to a further aspect of the invention, a chemical oxygen generator as described in the introductory portion is provided wherein a starter unit for initiating a chemical reaction is provided, said starter unit being a piezoelectrical unit for producing an initiating spark. It is to be understood that this chemical oxygen generator may in particular be designed and have single or a plurality of features of the embodiments as explained beforehand.

The provision of a piezoelectrical unit for producing an initiating spark to directly start the chemical reaction of the solid oxygen source provides superior capabilities and properties when compared to the pyrolytic ignition according to the prior art. First, the piezoelectric ignition does not comprise explosive or pyrolytic material and thus is in a lower class of risk than the pyrolytic ignition. Second, the piezoelectric ignition allows for a better control of the ignition process in that an electrical current occurs in the course of ignition which can be influenced by conventional control means like switches and the like. Thus, a central control of the ignition is possible and misuse can be prevented. For example, the ignition circuit can be equipped with a switch which is activated by a central control unit and this switch can for example be open in regular flight condition and activated to be closed in case of an emergency situation. Such switch may be present at each emergency oxygen device of an aircraft and may further be actuated by a central unit, e.g. closed to allow ignition of the oxygen generator. By this, misuse of the emergency oxygen system and accidental activation of the oxygen supply by a passenger can safely be prevented.

According to a further aspect of the invention, a flow control unit is integrated into said housing or directly attached to said housing via a flange. Such a flow control unit will provide an acceptable flow rate and pressure of the oxygen out of the oxygen generator and the integration or direct mounting of such control unit to the oxygen generator provides a compact design of the oxygen generator.

A further aspect of the invention is an emergency oxygen device having one or a plurality of oxygen masks for providing oxygen to a passenger or cabin crew including an oxygen generator according to the embodiments described before hand. Such emergency oxygen device may additionally include a control unit arranged in the flow path between the oxygen generator and the oxygen masks and adapted to control the flow rate and/or pressure of the oxygen delivered to the oxygen mask. Such control unit may use an ambient pressure or a signal from a central sensor or control unit as input signal.

A further aspect of the invention is a manufacturing method for manufacturing a chemical oxygen generator wherein a solid material which is able to produce oxygen in a chemical reaction is attached to a hollow tube in an isostatic pressing procedure in such a way that the hollow tube is embedded in the solid material. The manufacturing method may be further improved in that the solid material and the hollow tube is mounted into a housing in such a way that a hollow space is provided between the outer, circumferential surface of the solid material and the inner surface of the housing. Using these manufacturing techniques, it is possible to manufacture an oxygen generator as described before hand and having the superior properties of the oxygen generator according to the invention.

Finally, a further aspect of the invention is a method for providing oxygen to a passenger or cabin crew in an emergency situation on board of an aircraft, wherein the oxygen is produced within an chemical oxygen generator by a chemical reaction of a solid material, said oxygen is introduced into a hollow tube embedded in said solid material through at least one, preferably a plurality of radial openings inside that hollow tube and directed to an outlet opening in a housing comprising said solid material. In a preferred embodiment of this method, the oxygen is directed out of the hollow tube at a second end of said housing, redirected into a hollow space between said solid material and said housing and flows through this hollow space to a first end of the housing, where it is directed through an outlet provided at said first end of the housing.

BRIEF DESCRIPTION OF THE DRAWINGS

Preferred embodiments of the invention are described with reference to the figures. In the figures.

DETAILED DESCRIPTION

Figure 1:
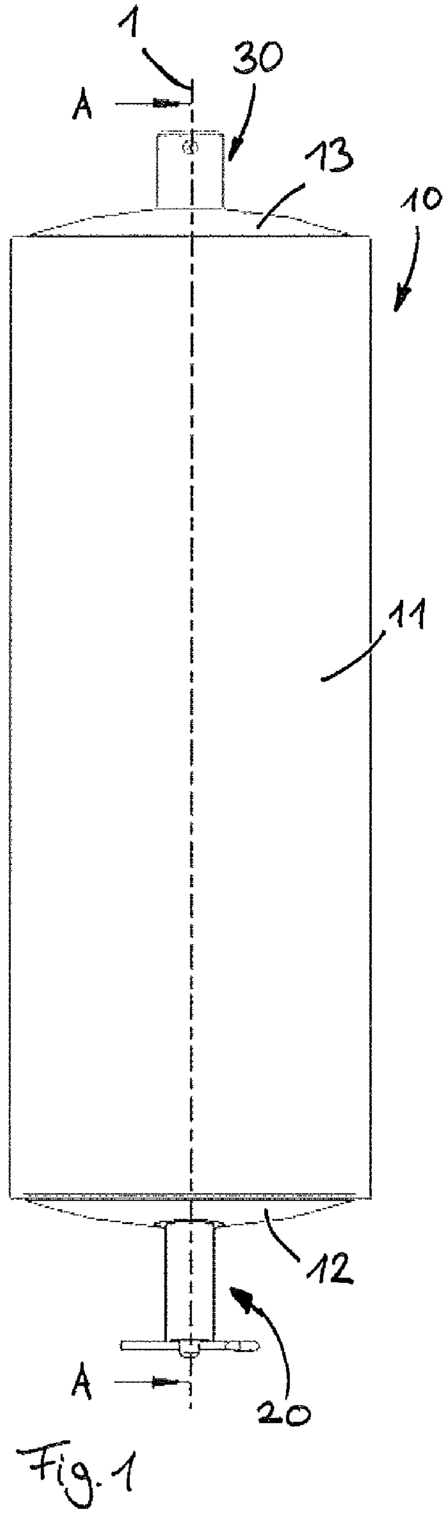
FIG. 1 shows a top view of an oxygen generator according to a first embodiment of the invention.

Referring first to FIG. 1, an oxygen generator according to a first embodiment of the invention comprises a cylindrical housing 10 extending along a longitudinal axis 1.

The housing 10 comprises a cylindrical wall 11, a front end cover 12 and a back end cover 13.

A piezoelectrical starter unit is attached to the front end cover 12.

An outlet conduct 30 is attached to the back end cover 13. The outlet conduct 30 comprises an axial portion 31 and a connector tube 32 having an outlet opening 33 for connecting a tube or hose to the oxygen generator for directing the oxygen to an oxygen mask.

Figure 2:
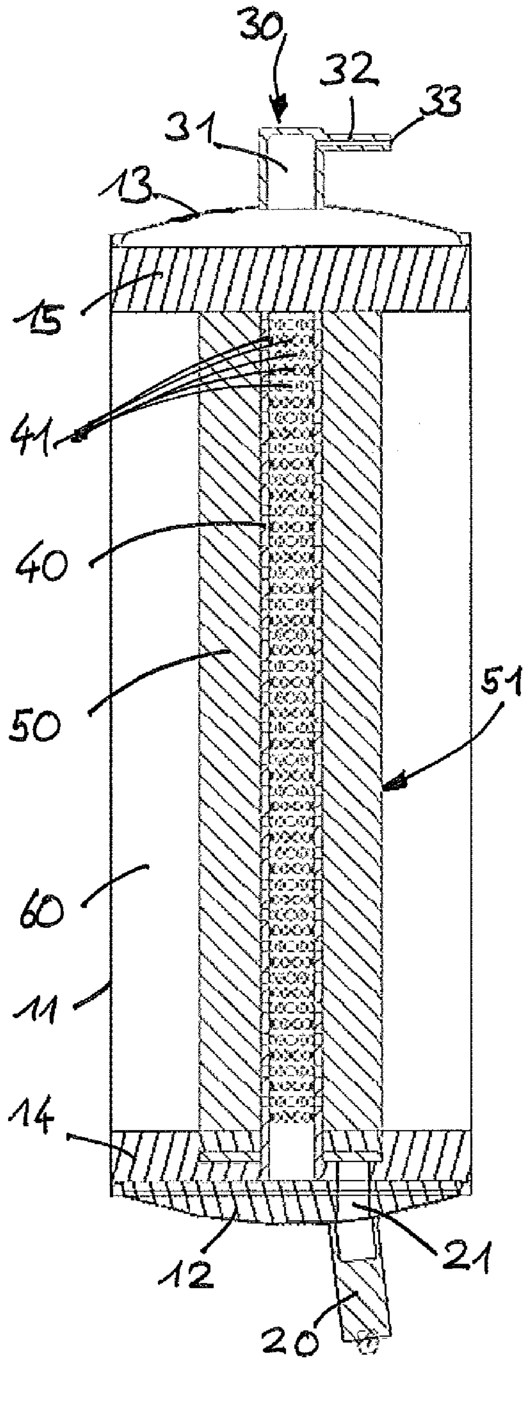
FIG. 2 shows a cross sectional side view along the line A-A in FIG. 1 of the embodiment of FIG. 1.

As can be seen in detail from FIG. 2, a hollow tube 40 extends along the longitudinal axis 1 inside the housing 10. The hollow tube 40 is arranged co-axis to the longitudinal axis 1. The hollow tube is perforated with a plurality of radial openings 41.

The hollow tube 40 is embedded in a solid oxygen source material 50 comprising sodium chlorate. Said solid oxygen source has a ring-shaped cross sectional area and extends about the whole length of the hollow tube 40.

The hollow tube 30 is centered within endside ring elements 14, 15 which outer diameter corresponds to the inner diameter of the cylindrical wall 11 of the housing 10. By this, the hollow tube 40 is fixed in a central position within the housing 10.

A hollow space 60 having a ring shaped cross section is provided between the outer circumferential surface 51 of the solid oxygen source and the inner surface of the cylindrical wall 11.

As can be seen in FIG. 2, the starter unit 20 is in direct contact with the solid oxygen source by way of an eccentric arrangement in distance to the longitudinal axis 1 of the housing 10 via a channel 21. By this, the chemical reaction can be started in a region adjacent to the front end cover 12 of the housing 10 in the solid oxygen source 50. Oxygen produced in this starting region can enter through the radial openings into the interior of the hollow tube 40 and flow along the longitudinal axis 1 to the outlet conduct 30. There it can leave the housing 10 and be directed via the outlet opening 33 to an oxygen mask, a control unit or the like. The hollow space 60 serves as an insulation for preventing high temperatures of the cylindrical wall 11 of the oxygen generator in course of the exothermic reaction of the solid oxygen source 50.

Figure 3:
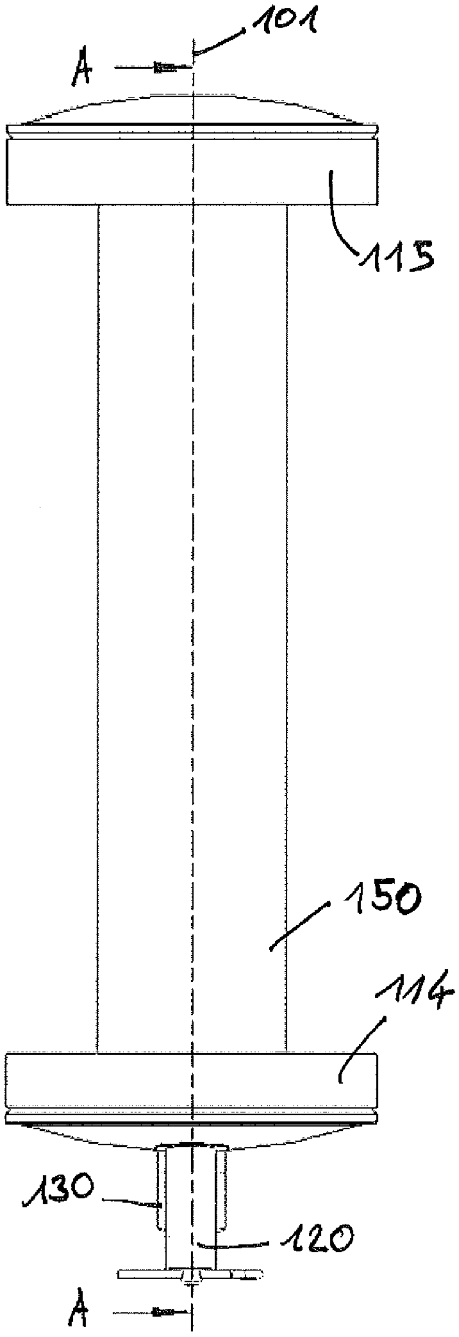
FIG. 3 shows a top view of an oxygen generator according a second embodiment of the invention wherein the housing is not shown for the purpose of better understanding.
Figure 4:
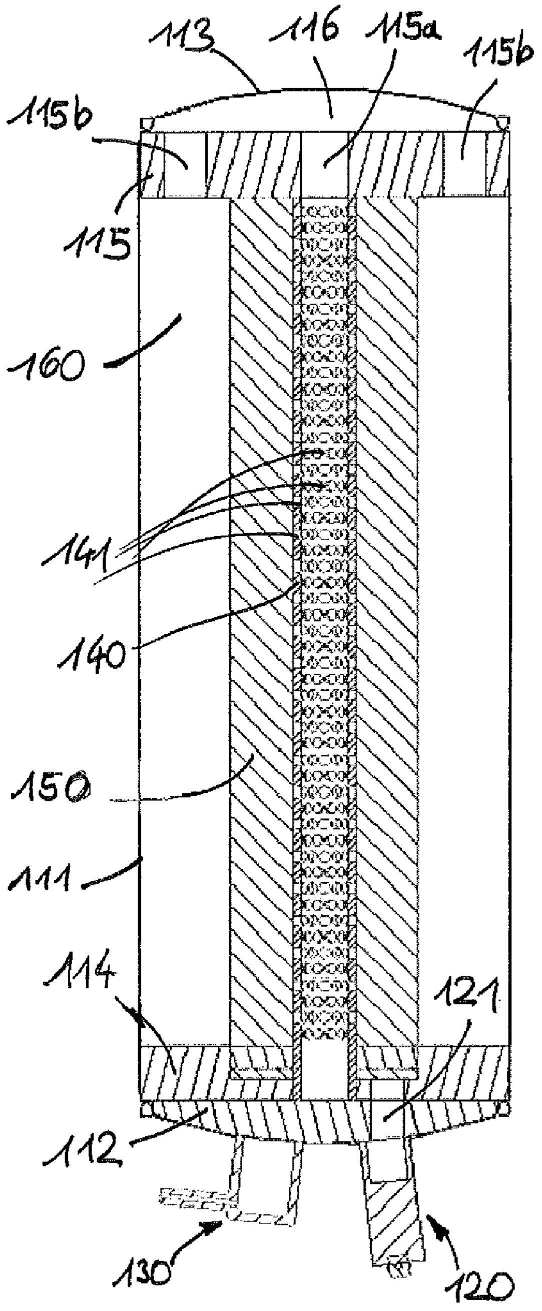
FIG. 4 shows a sectional side view along line A-A in FIG. 3 of the embodiment shown in FIG. 3.

FIGS. 3 and 4 show a second embodiment of the invention. In the second embodiment, a hollow tube 140 embedded in a solid oxygen source 150 is provided in a similar arrangement as in the first embodiment of the FIGS. 1 and 2. Still further, said hollow tube 140 is positioned within a housing (not shown) by way of ring-shaped elements 114, 115, the outer diameter of which corresponding to the inner surface of a cylindrical wall 111 of the housing in a similar design as shown in FIGS. 1 and 2.

A starter unit 120 is arranged at a front end cover 112 and is in contact to the solid oxygen source 150 via a channel 121.

In contrast to the first embodiment of FIGS. 1 and 2, the second embodiment shown in FIGS. 3 and 4 has an outlet conduct 130 which is arranged at the front end cover 112, i.e. at the same end like the starter unit 120.

The back end cover 113 of the second embodiment is a closed cover with a slightly convex shape. It defines a flow chamber 116 which is in fluid communication with a central opening 115*a* in the ring-shaped element 115 and a plurality of eccentric openings 115*b* in said ring-shaped element 115. The openings 115*a* and *b* are oriented in an axial direction parallel to the longitudinal axial 101 of the oxygen generator. The central opening 115*a* is in fluid communication with the interior of the hollow tube 140. The eccentric openings 115*b* are in fluid communication with a hollow space 160 located between the solid oxygen source 150 and the cylindrical wall 111 of the housing.

Upon ignition and start of the chemical reaction by the starter unit 120 oxygen is produced close to the front end cover 112 in the solid oxygen source 150. The oxygen enters the interior of the hollow tube 140 through the perforations 141 and flows from the front end cover 112 to the back end cover 113. The oxygen enters through the central opening 115*a* into the hollow space 116 and returns through the eccentric openings 115*b* into the hollow space 160. The oxygen flows through the ring-shaped hollow space 160 back to the frontend cover 112 and enters into the outlet conduct 130 through a channel in the ring-shaped element 114 and the front end cover 112 which channel is not shown in the cross section according to FIG. 4.

The primary advantage of the embodiment of FIG. 3, 4 is the oxygen flowing along the inner side and the outer side of the solid oxygen source and thus transferring more heat into said solid oxygen source than the oxygen of the first embodiment. By this, the chemical reaction can be started up quicker whereas a slight increase of the temperature of the outer housing 111 must be taken into account in the second embodiment.

The invention claimed is:

1. Chemical oxygen generator for an emergency oxygen device, comprising:

an outer housing defining an interior space and comprising an outlet opening for directing oxygen out of the interior space, a solid oxygen source within said interior space containing a material comprising sodium chlorate which is able to produce oxygen in a chemical reaction, a hollow tube within said interior space embedded in said solid oxygen source, wherein the hollow tube and the solid oxygen source extend from a first end of the outer housing to a second end of the outer housing, wherein the hollow tube comprises a plurality of radial openings that form a perforated hollow tube, and a starter unit in contact with the solid oxygen source at a starting region located near the first end of the outer housing, the starter unit for producing an initiating spark that initiates a chemical reaction in the solid oxygen source to produce oxygen at the starting region, wherein the produced oxygen enters the hollow tube.

2. The chemical oxygen generator according to claim 1, wherein the outer housing defines a longitudinal direction and a transversal direction and has a larger extension in the longitudinal direction than in the transversal direction and wherein the hollow tube extends along the longitudinal direction.

3. The chemical oxygen generator according to claim 1, wherein the hollow tube is made from metal.

4. The chemical oxygen generator according to claim 1, wherein the outlet opening is located at the second end of the outer housing.

5. The chemical oxygen generator according to claim 1, wherein the starter unit and the outlet opening are mounted at the first end of the outer housing.

6. The chemical oxygen generator according to claim 1, wherein a hollow space is located between the solid oxygen source and the outer housing and wherein the hollow space is in fluid communication with an interior of the hollow tube.

7. The chemical oxygen generator according to claim 6, wherein the fluid communication between the hollow space and the hollow tube is provided at the second end of the outer housing which is opposed to the first end.

8. The chemical oxygen generator according to claim 1, wherein a filter for filtering chlorine is integrated into said hollow tube.

9. The chemical oxygen generator according to claim 1, wherein said solid oxygen source extends from the first end of the outer housing to the second end of the outer housing along said hollow tube, a hollow space is provided between said solid oxygen source and said outer housing, said hollow space being in fluid communication with the interior space of said hollow tube at a second end of said solid oxygen source to direct oxygen from said interior space of said hollow tube into said hollow space, said outlet opening is located at a first end of the solid oxygen source and is in fluid communication with said hollow space.

10. The chemical oxygen generator according to claim 1, wherein a flow control unit is integrated into said outer housing or directly attached to said outer housing via a flange.

11. Emergency oxygen device for passenger or cabin crew of an aircraft, comprising, a source of oxygen, at least one oxygen mask connected to said source of oxygen and adapted to be worn by a passenger to direct oxygen to mouth and/or nose of the passenger, wherein the oxygen source is a chemical oxygen generator comprising an outer housing defining an interior space and comprising an outlet opening for directing oxygen out of the interior space, a solid oxygen source within said interior space containing a material comprising sodium chlorate which is able to produce oxygen in a chemical reaction, a hollow tube within said interior space embedded in said solid oxygen source, wherein the hollow tube and the solid oxygen source extend from a first end of the outer housing to a second end of the outer housing, wherein the hollow tube comprises a plurality of radial openings that form a perforated hollow tube, and a starter unit in contact with the solid oxygen source at a starting region located near the first end of the outer housing, the starter unit for producing an initiating spark that initiates a chemical reaction in the solid oxygen source to produce oxygen at the starting region, wherein the produced oxygen enters the hollow tube.

12. The chemical oxygen generator according to claim 6, wherein the hollow space comprises a ring-shaped space.

13. The chemical oxygen generator according to claim 1, wherein the starter unit comprises a piezoelectrical starter unit.

14. The chemical oxygen generator according to claim 1, wherein the oxygen produced by the starter unit is delivered to the hollow tube for generation of additional oxygen to be released through the outlet.

15. A chemical oxygen generator for an emergency oxygen device, comprising:

an outer housing defining an interior space;

a solid oxygen source within said interior space containing a material comprising sodium chlorate which is able to produce oxygen in a chemical reaction, the solid oxygen source being in fluid communication with one single opening in the outer housing for directing oxygen out of the interior space;

a hollow tube within said interior space embedded in said solid oxygen source, wherein the hollow tube and the solid oxygen source extend from a first end of the outer housing to a second end of the outer housing, wherein the hollow tube comprises a plurality of radial openings that form a perforated hollow tube, and a starter unit in contact with the solid oxygen source near the first end of the outer housing, the starter unit for producing an initiating spark that initiates a chemical reaction in the solid oxygen source to produce oxygen, wherein the produced oxygen enters the hollow tube.

* * * * *